US00PP33435P2

(12) United States Plant Patent
van Kesteren

(10) Patent No.: US PP33,435 P2
(45) Date of Patent: Aug. 31, 2021

(54) ***DELPHINIUM* PLANT NAMED 'COADELBBL'**

(50) Latin Name: ***Delphinium* hybrid**
Varietal Denomination: COADELBBL

(71) Applicant: Anthony Paul Coakley, Glasgow (GB)

(72) Inventor: Marc van Kesteren, Noordwijkerhout (NL)

(73) Assignee: Paul Anthony Coakley, Gravenzande (NL)

( * ) Notice: Subject to any disclaimer, the term of this patent is extended or adjusted under 35 U.S.C. 154(b) by 0 days.

(21) Appl. No.: 17/077,608

(22) Filed: Oct. 22, 2020

(51) Int. Cl.
*A01H 5/02* (2018.01)
*A01H 6/72* (2018.01)

(52) U.S. Cl.
USPC ..... Plt./423
CPC ..... *A01H 6/72* (2018.05)

(58) Field of Classification Search
USPC ..... Plt./423
CPC ..... A01H 6/72; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Delphinium* hybrid plant named 'COADELBBL' which is characterized by basal foliage and a compound terminal raceme held above the foliage, flowers loosely held on long pedicels, flowers with an abundance of tepaloids, a unique color appearance of the perianth comprised of a light green center that is very lightly tipped violet and becoming progressively suffused with light pink towards the outer whorls of the perianth with a violet-blue outer whorl of the perianth, and the stability and uniformity of these traits through successive cycles of asexual propagation.

3 Drawing Sheets

Latin name of the genus and species: The Latin name of the genus and species of the novel variety disclosed herein is *Delphinium* hybrid.

Variety denomination: The inventive variety of *Delphinium* disclosed herein has been given the variety denomination 'COADELBBL'.

BACKGROUND OF THE INVENTION

Parentage: The claimed plant originated as a naturally occurring, whole-plant mutation of *Delphinium* hybrid 'Coadelbol' (U.S. Plant Pat. No. 27,704). In the summer of 2012 the inventor discovered the mutation at a commercial greenhouse in Noordwijkerhout, Netherlands, growing amongst a crop of *Delphinium* hybrid 'Coadelbol'. The mutation was noted for its unique light pink flower color and was subsequently isolated for further evaluation in order to confirm the distinctness and stability of the characteristics first observed.

Asexual Reproduction: In the spring of 2015, 'COADELBBL' was first asexually reproduced in Glasgow, Scotland by way of softwood stem cuttings. The claimed plant was found to asexually reproduce in uniform and stable manner and four successive cycles of vegetative propagation have proven to be true to type.

SUMMARY OF THE INVENTION

The following characteristics have been repeatedly observed and represent the distinguishing characteristics of the new *Delphinium* plant, 'COADELBBL'. These traits, in combination, distinguish 'COADELBBL' as a new and distinct cultivar.

1. 'COADELBBL' exhibits basal foliage with a compound terminal raceme held above the foliage; and 2. 'COADELBBL' exhibits flowers loosely held on long pedicels along the raceme; and
3. 'COADELBBL' exhibits an abundance of tepaloids; and
4. 'COADELBBL' exhibits flowers with multiple whorls of tightly held tepaloids at the center of the perianth, somewhat more relaxed tepaloids towards the outer whorls of the perianth, and an outer whorl of loosely held tepals; and
5. 'COADELBBL' exhibits violet-blue tepals when fully opened; and
6. 'COADELBBL' exhibits outermost tepaloids that are colored violet with violet-purple suffusion on the inner surface, and violet-blue with violet suffusion on the outer surface when fully opened.
7. 'COADELBBL' exhibits tepaloids at and near the center of the perianth which are light green-white with light violet suffusion, becoming greyed-violet at and near the apex; and
8. 'COADELBOL' exhibits a unique color appearance of the perianth comprised of a light green center that is very lightly tipped light pink, becoming progressively more suffused with light pink towards the outer whorls of the perianth, and eventually transitioning to violet-blue at the outer whorl of the perianth.

BOTANICAL DESCRIPTION OF THE PLANT

Figure 1:
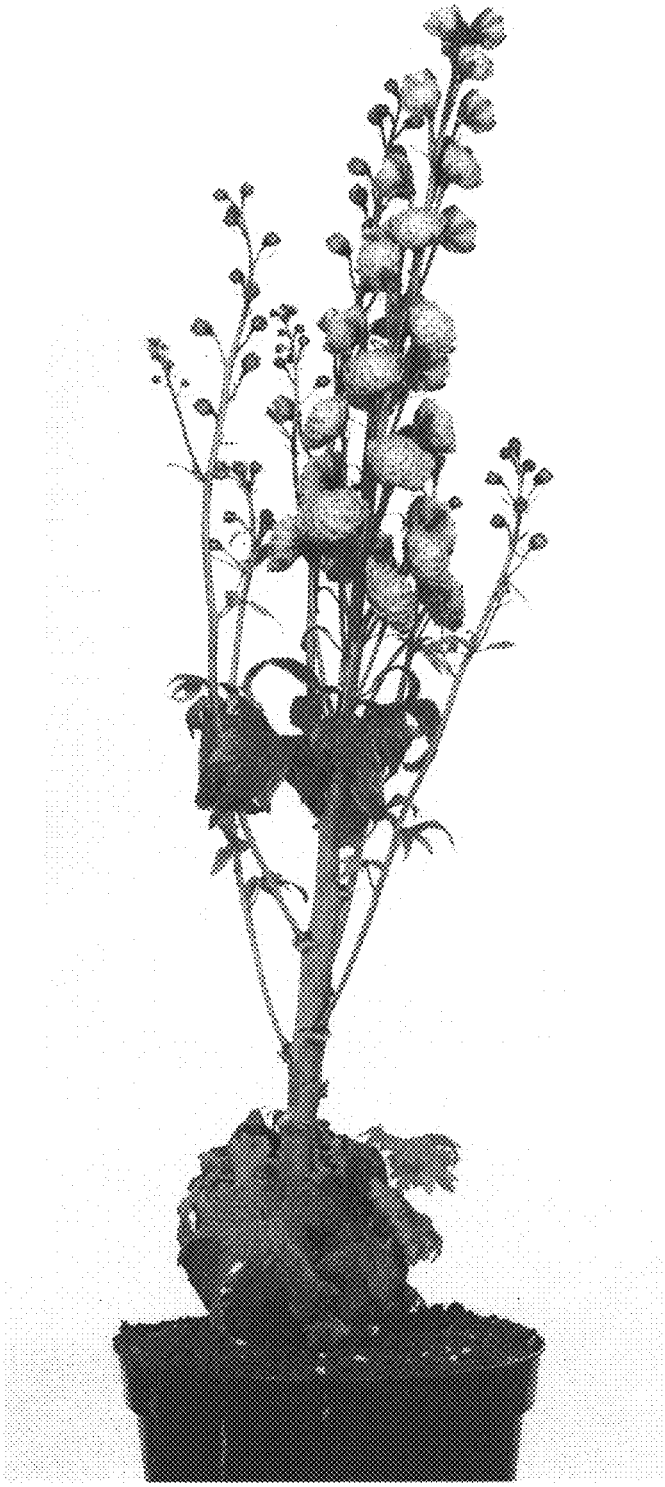
FIG. 1 illustrates, as nearly true as it is reasonably possible to make the same in color photographs of this type, an exemplary 'COADELBBL' plant at approximately 6 months of age grown in Glasgow, Scotland.
Figure 2:
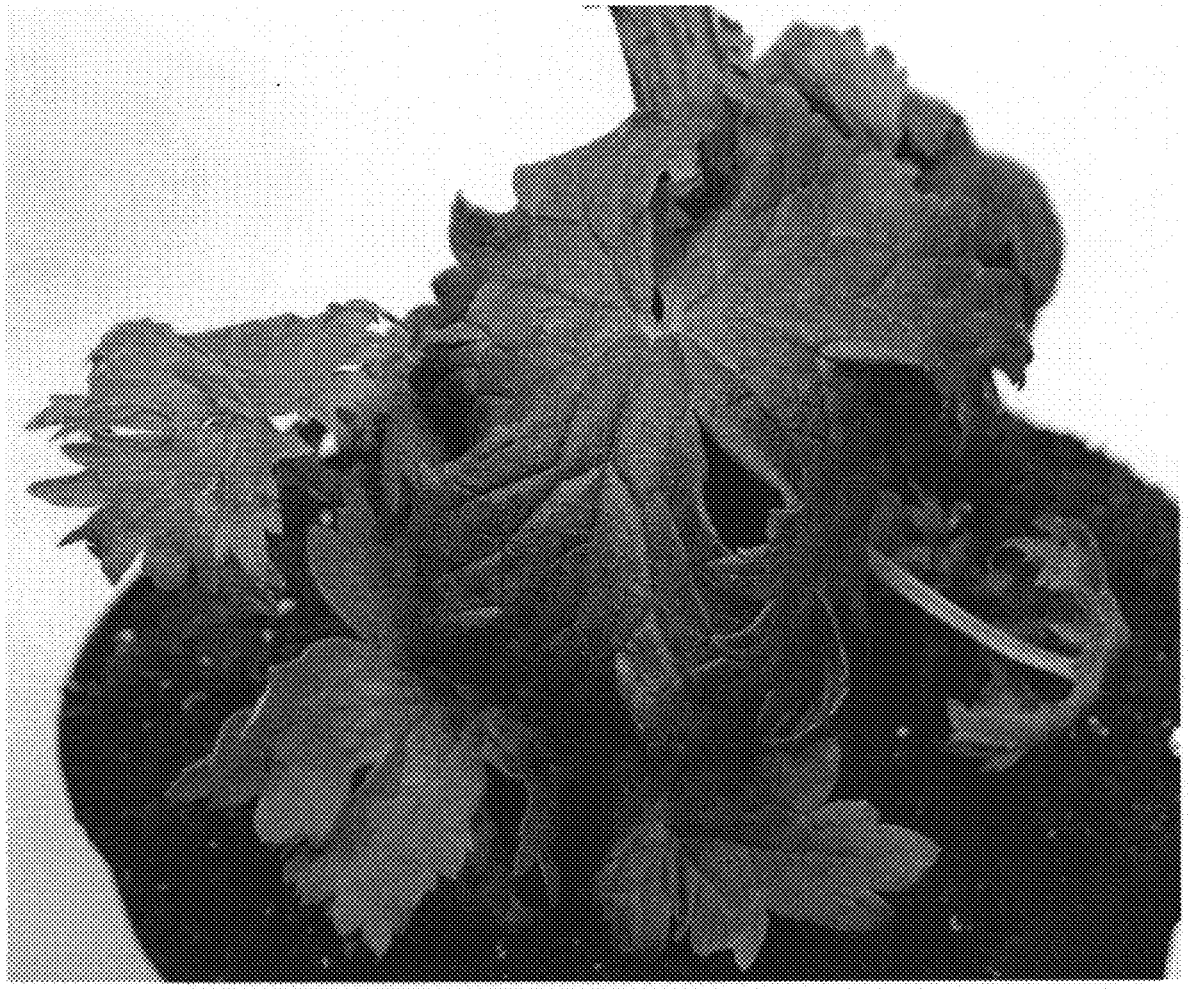
FIG. 2 illustrates, as nearly true as it is reasonably possible to make the same in color photographs of this type, the foliage of 'COADELBBL'.
Figure 3:
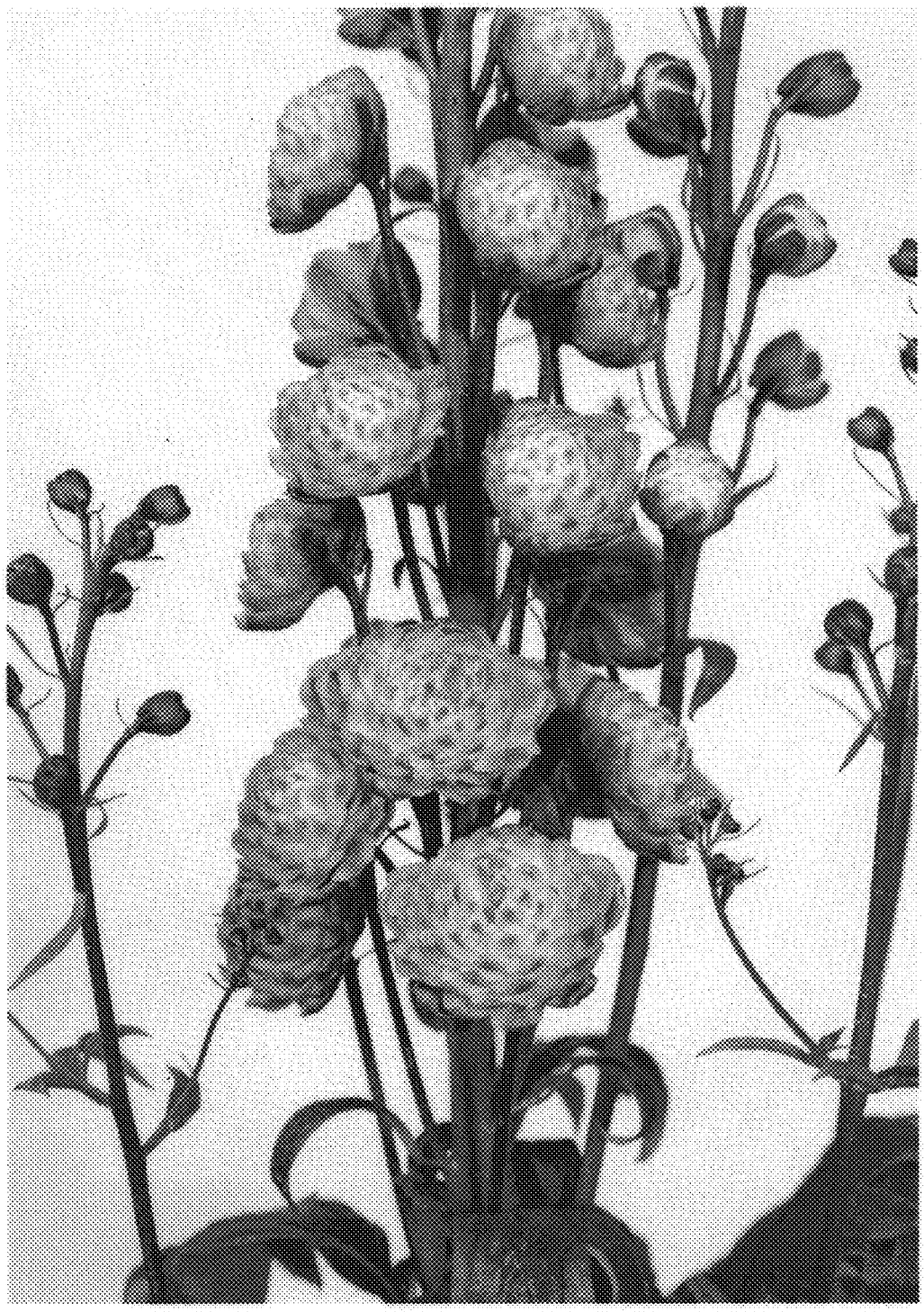
FIG. 3 illustrates, as nearly true as it is reasonably possible to make the same in color photographs of this type, the flowers of 'COADELBBL'.

The following is a detailed botanical description of a new and distinct *Delphinium* plant known as 'COADELBBL'. Plant observations were made on a 6 month-old plant growing in Glasgow, Scotland. The observed plant was field-grown in full exposure to natural sunlight, maintained with organic fertilizer and overhead irrigation. Chemical control of powdery mildew was utilized in production but no other pest or pathogen countermeasures were employed. For the purposes of these observations, the observed plant was harvested from the field and potted into a 19 cm nursery container. Observation data was recorded in July of 2020.

Those skilled in the art will appreciate that certain characteristics will vary with older or, conversely, younger plants. 'COADELBBL' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, Sixth Edition except where common terms of color are used.

A botanical description of 'COADELBBL' and comparisons with the parent and most similar commercial cultivar are provided below.

General plant description:

- *Plant habit*.—Perennial plant with basal foliage and branched flowering stems, bearing flowers arranged on terminal racemes held above the foliage.
- *Plant profile*.—Narrow ovate to ovate.
- *Height*.—33.7 cm to the top of the foliar plane; 68.0 cm to the top of the floral plane.
- *Spread*.—23.0 cm.
- *Plant vigor*.—Moderately vigorous.
- *Growth rate*.—Moderately fast growing.
- *Propagation*.—Method — Softwood stem cuttings. Time to initiate rooting — 6 weeks at an average ambient temperature of 15 degrees Celsius. Time to produce flowering plant from rooted cutting — Approximately 6 months in an 11 cm container.
- *Pest resistance and susceptibility*.—Not any more or less susceptible to pests or diseases known to effect *Delphinium* sp.
- *Environmental tolerances*.—Adapt to, at least, USDA Zones 5 to 9 and temperatures ranging from minus 23 degrees Celsius to 35 degrees Celsius; moderate tolerance to rain; low tolerance to wind.

Root system:

- *Description*.—A moderately dense network of relatively shallow thin, fibrous feeder roots and deeper thick anchor roots.

Stems:

- *Branching habit*.—No vegetative branches are present, however branched flowering stems are present.
- *Flowering stem*.—Quantity — Two. Attitude — Erect; near vertical. Aspect — Generally rounded; slightly angular. Strength — Strong. Length — 17.1 cm. Diameter — 1.6 cm. Internode length — 1.7 cm. Texture — Lightly pubescent; hairs are 0.1 cm on average and are colored a translucent white, nearest to RHS NN155C. Luster — Matte, due to the presence of epicuticular wax. Color, developing stems — Yellow-green, nearest to RHS 144B. Color, mature stems — Yellow-green, nearest to a combination of RHS 146A and 146B, and covered with an epicuticular wax which is colored nearest to in between green and yellow-green, RHS 138B and 144B. Color at the internodes — Yellow-green, nearest to a combination of RHS 146A and 146B, and covered with an epicuticular wax which is colored nearest to in between green and yellow-green, RHS 138B and 144B.

Foliage:

- *Arrangement*.—Alternate.
- *Attachment*.—Petiolate.
- *Division*.—Simple.
- *Quantity*.—14 stem leaves.
- *Shape*.—Palmate with a reniform outline; deeply lobed to near cleft.
- *Lobes*.—Depth of sinuses — Deep. Sinus orientation — Convergent.
- *Aspect*.—Slightly convex and reflexed.
- *Attitude*.—Outward.
- *Length*.—17.3 cm.
- *Width*.—19.9 cm.
- *Apex*.—Acute to narrowly acute.
- *Base*.—Hastate; lobes free to touching.
- *Margins*.—Coarsely serrate; sparsely pubescent.
- *Texture and pubescence, adaxial surface*.—Smooth and glabrous.
- *Texture and pubescence, abaxial surface*.—Smooth and glabrous.
- *Luster, adaxial surface*.—Matte.
- *Luster, abaxial surface*.—Matte.
- *Color*.—Juvenile foliage color, adaxial surface — Nearest to in between green and yellow-green, RHS 143A and 144A. Juvenile foliage color, abaxial surface — Yellow-green, nearest to RHS 146B. Mature leaf color, adaxial surface — Nearest to in between green and yellow-green, RHS NN137A and 144A. Mature leaf color, abaxial surface — Yellow-green, nearest to RHS 147B.
- *Venation*.—Type — Laciniate. Vein color, adaxial surface — Yellow-green, nearest to RHS 144A. Vein color, abaxial surface — Yellow-green, nearest to a mixture of RHS 146C and 146D.
- *Petiole*.—Length — 7.1 cm. Diameter — Petioles are flattened; 0.4 cm tall and 0.5 cm wide. Strength — Very strong. Texture, adaxial and abaxial surfaces — Smooth and glabrous. Luster, adaxial and abaxial surfaces — Moderately glossy. Color, adaxial and abaxial surface — Yellow-green, nearest to RHS 146A.
- *Stipules*.—Absent.

Inflorescence:

- *Inflorescence type*.—Compound terminal raceme with a central, main raceme and multiple lateral racemes.
- *Natural flowering season*.—Late summer in Glasgow, Scotland.

*Time to flower or response time*.—Approximately 10 months.

*Height*.—The entire compound raceme is 50.8 cm high, from the lowest branching of the peduncle to the apex of the inflorescence. The main, central raceme is 37.8 cm tall.

*Diameter*.—The entire compound raceme is 21.9 cm in diameter; the main, central raceme is 9.3 cm in diameter.

*Quantity of flowers per inflorescence*.—140 on the entire compound raceme; 29 on the main raceme.

*Peduncle*.—Length — Approximately 33.4 cm. Diameter — Approximately 0.65 cm. Attitude — Erect, in an average angle of 0 degrees to the main stem. Strength — Strong. Texture — Smooth and glabrous. Luster — Slightly glossy. Color — Yellow-green, nearest to RHS 146B.

*Bracts*.—Quantity — Two bracts are present at the base of each individual flower. Shape — Linear. Length — 1.4 cm, on average. Width — 0.1 cm, on average. Apex — Narrowly acute. Base — Cuneate. Margin — Entire. Texture — Smooth and sparsely covered with short, soft hairs with an average length of 0.8 mm and colored white, nearest to RHS NN155C. Color, adaxial and abaxial surfaces — Yellow-green, nearest to a mixture of RHS 144A and 144B.

Flower bud:

*Shape*.—Broad obovate.

*Length*.—Average of 1.4 cm.

*Diameter*.—1.1 cm tall and 0.9 cm wide.

*Texture*.—Smooth and sparsely pubescent; soft white hairs are approximately 0.04 cm long and colored a translucent white, nearest to RHS NN155C.

*Luster*.—Slightly glossy.

*Color, upper surface*.—Violet, nearest to a mixture of RHS 86A and 86B.

*Color, lower surface*.—Yellow-green, nearest to RHS 145C, and lightly suffused with violet, nearest to a mixture of RHS N88C and N88D.

Flower:

*Type and form*.—Rotate; double.

*Aspect*.—Outwardly to slightly upright.

*Flowering habit*.—Freely flowering.

*Flower longevity on plant*.—Approximately 10 days.

*Longevity of cut flowers*.—Approximately 10 days.

*Persistent or self-cleaning*.—Self-cleaning.

*Fragrance*.—Non-fragrant.

*Diameter*.—Average of 4.7 cm.

*Depth*.—Average of 2.3 cm.

*Perianth*.—No distinct petals and sepals, only tepals and tepaloids are present. Tepals — Quantity — 5 unfused tepals; one dorsal, two lateral, and two lower tepals. Arrangement — Rotate; single whorl. Attitude — Relaxed. Aspect — Moderately concave. Length — Dorsal tepal — 2.5 cm. Lateral tepals — 2.3 cm. Lower tepals — 2.4 cm. Width — Dorsal tepal — 1.6 cm. Lateral tepals — 1.85 cm. Lower tepals — 1.6 cm. Shape — Dorsal tepal is broad elliptic; lateral and lower tepals are broad obovate. Apex — All tepals are broad acute. Base — All tepals are broad cuneate. Margin — All tepals are entire and moderately undulated. Texture, luster and pubescence of the upper surface — All tepals are glabrous, velvety, and matte. Texture, luster and pubescence of the lower surface — All tepals are glabrous, velvety, and matte. Color when opening, upper surface — Dorsal tepal — Violet, nearest to RHS N88C, and fading to yellow-green towards the base, nearest to in between RHS 144B and 146D; margins along the distal half of the tepal are yellow-green, nearest to a mixture of RHS 145C and 145D. Lateral tepals — Violet-blue, nearest to RHS 98B, and fading to violet-blue towards the margins and apex, nearest to a mixture of RHS 90C and 90D; proximal margins and base are yellow-green, nearest to RHS 145D. Lower tepals — Violet-blue, nearest to RHS 98B, and fading to violet-blue towards the margins and apex, nearest to a mixture of RHS 90C and 90D; proximal margins and base are yellow-green, nearest to RHS 145D. Color when opening, lower surface — Dorsal tepal — Violet, nearest to RHS 86B, and fading to yellow-green towards the base, nearest to RHS 147A; apex is nearest to in between violet-blue and brown, RHS N92A and N200A. Lateral tepals — Violet-blue, nearest to RHS 90D, with a greyed-green central blotch, nearest to RHS 197A; proximal margins are yellow-green, nearest to RHS 145D; fading to yellow-green at the base, nearest to RHS 145D. Tepals are veined violet-blue, nearest to a mixture of RHS N89A and N89B. Lower tepals — Violet-blue, nearest to RHS 90C, and fading to greyed-green towards the apex, nearest to RHS 197A; suffused with yellow-green, nearest to RHS 147B; fading to green towards the base, nearest to RHS 141B. Tepal veined violet-blue, nearest to RHS N89B. Color when fully opened, upper surface — Dorsal tepal — Violet, nearest to RHS 96C, and fading to violet-blue towards the margins and base, nearest to a mixture of RHS 91A and 91B; fading to yellow-green at the base, nearest to in between RHS 145A and 146D. Tepals do not fade with age. Lateral tepals — Violet-blue, nearest to RHS 96C, and fading to violet-blue towards the margins, nearest to a mixture of RHS 91A and 91B; fading to yellow-green at the base, nearest to in between RHS 145A and 146D. Tepals do not fade with age. Lower tepals — Violet-blue, nearest to RHS 96C, and fading to violet-blue towards the margins, nearest to a mixture of RHS 91A and 91B; fading to yellow-green at the base, nearest to in between RHS 145A and 146D. Tepals do not fade with age. Color when fully opened, lower surface — Dorsal tepal — Violet-blue, nearest to RHS 93C; fading to yellow-green towards the base, nearest to RHS 146A; fading to yellow-green towards the apex, nearest to in between RHS 147A and 147B. Tepals do not fade with age. Lateral tepals — Violet-blue, nearest to RHS 90D, and fading to violet-blue towards the margins, nearest to a mixture of RHS 96C and 96D; fading to yellow-green at the base, nearest to a mixture of RHS 145A and 145B; a yellow-green central blotch is present near the apex, nearest to RHS 146A. Tepals are veined violet-blue, nearest to a mixture of RHS N89A and N89B. Tepals do not fade with age. Lower tepals — Violet-blue, nearest to RHS 94B, and fading to yellow-green towards the base, nearest to RHS 144B; a yellow-green blotch is present near the apex, nearest to in between RHS 146C and 146D. Tepals do not fade with age. Tepal venation color — Fully opened, upper surface — No venation visible. Fully opened, lower surface — Violet-blue, nearest to RHS N89C. Tepaloids — Arrangement — Rotate; the unfused tepaloids are relatively tightly-held in 7 whorls. Attitude — Erect. Aspect — Strongly concave. Quantity — 55. Length — 2.1 cm. Width — 1.2 cm. Shape — Outer tepaloids are elliptic and becoming obovate towards the center of the perianth. Apex — Outer tepaloids are broad acute and becoming obtuse towards the center of the perianth. Base — Broad cuneate. Margin — Entire; slightly undulated. Texture, luster and pubescence of the inner surface — Velvety, glabrous and slightly glossy. Texture, luster and pubescence of the outer surface — Velvety, glabrous and matte. Color when opening, upper surface — Outer tepaloids are green-white, nearest to RHS 157D, with a yellow-green central blotch, nearest to RHS 145C. Inner tepaloids are green-white, nearest to RHS 157D yet lighter, and fading to yellow-green at the apex, nearest to RHS 145C. Color when opening, lower surface — Outer tepaloids are green-white, nearest to RHS 157D, with a yellow-green central blotch, nearest to a mixture of RHS 145B and 145C; apices of outer tepaloids are greyed-green, nearest to RHS 197D. Inner tepaloids are green-white, nearest to RHS 157D yet lighter, and fading to yellow-green at the apex, nearest to RHS 145C. Color when fully opened, upper surface — Outer tepaloids are violet, nearest to RHS N87D, and suffused with violet-purple, nearest to RHS 94B; a yellow-green central blotch is present, nearest to RHS 145B. Inner tepaloids are white, nearest to RHS N155B, with a greyed-green central blotch, nearest to RHS 197B. Tepaloids do not fade with age. Color when fully opened, lower surface — Outermost tepaloids are violet-blue, nearest to RHS 96D, and suffused with violet, nearest to a mixture of RHS N88B and N88C; margined violet-blue, nearest to a mixture of RHS 96B and 96C. Inner tepaloids are green-white, nearest to RHS 157D, and suffused with violet, nearest to RHS 85B; distal portion of the tepaloid fading to greyed-violet, nearest to RHS 197B. Tepaloids do not fade with age. Tepaloid venation color when fully opened, inner surface — Yellow-green, nearest to RHS 147C. Tepaloid venation color when fully opened, outer surface — No venation visible. Pedicels — Length — 6.8 cm. Diameter — 0.2 cm. Angle — Average angle to peduncle axis is approximately 20 degrees. Strength — Moderately strong to strong. Texture — Smooth and glabrous. Luster — Glossy. Color — Yellow-green, nearest to in between RHS 144A and 146B. Spurs — Quantity — One dorsal tepal spur present. Length — 0.6 cm. Diameter — 0.3 cm. Shape — Broad oblong. Apex — Obtuse. Base — Broad cuneate. Texture — Moderately rugose and glabrous. Luster — Moderately glossy. Color — Yellow-green, nearest to RHS 148A.

Reproductive organs: All reproductive organs reduced to tepaloids. An undeveloped ovary is present; colored yellow-green, nearest to RHS 147A yet darker.

Fruit and seed: No fruiting has been observed.

Comparison With the Parent Plant

Plants of the new cultivar 'COADELBBL' differ from the parent, *Delphinium* hybrid 'COADELBOL' (U.S. Plant Pat. No. 27,704), by the characteristics described in Table 1.

TABLE 1

| Characteristic | 'COADELBBL' | 'COADELBOL' |
|---|---|---|
| Plant size. | Smaller than 'COADELBOL'. | Larger than 'COADELBBL'. |
| Abundance of foliage. | Less abundant than 'COADELBOL'. | More abundant than 'COADELBBL'. |
| Inflorescence type. | Compound terminal raceme. | Unbranched terminal raceme. |
| Inflorescence size. | Larger than 'COADELBOL'. | Smaller than 'COADELBBL'. |
| General appearance of the inflorescence. | Flowers appear to be more loosely held on the raceme due to longer flower pedicels. | Flowers appear to be more tightly held on the raceme due to shorter flower pedicels. |
| Tepaloid arrangement within the perianth. | Tepaloids are more tightly held in whorls. | Tepaloids are more loosely held in whorls. |
| Quantity of tepaloids. | Fewer than 'COADELBOL'. | Less than 'COADELBBL'. |
| General coloration of the outer tepaloids when fully opened. | Violet suffused with violet-purple to violet-blue suffused with violet. | Central zone of the tepaloids are violet; marginal zone is violet blue. |
| Expression of color on the tepaloids. | More subtle than 'COADELBOL'. | More prominent than 'COADELBBL'. |

Comparison With the Most Similar *Delphinium* Cultivar Known to the Inventor

Plants of the new cultivar 'COADELBBL' are most similar to the commercial cultivar, *Delphinium* hybrid 'COADELPNK' (a United States Patent application for which is being filed concurrently with the instant application). A comparison of 'COADELBBL' with *Delphinium* 'COADELPNK' is described in Table 2.

TABLE 2

| Characteristic | 'COADELBBL' | 'COADELPNK' |
|---|---|---|
| Plant size. | Smaller than 'COADELPNK'. | Larger than 'COADELBBL'. |
| Length of flowering stem. | Longer than 'COADELPNK'. | Shorter than 'COADELBBL'. |
| Inflorescence size. | Smaller than 'COADELPNK'. | Larger than 'COADELBBL'. |
| General coloration of the tepals when fully opened. | Violet-blue. | Light greyed-red to greyed-purple, generally appearing as a light pink coloration. |
| General coloration of the outer tepaloids when fully opened. | Violet suffused with violet-purple to violet-blue suffused with violet. | Light greyed-red to greyed-purple, generally appearing as a light pink coloration. |
| Quantity of tepaloids. | Fewer than 'COADELPNK'. | More than 'COADELBBL'. |

That which is claimed is:

1. A new and distinct variety of *Delphinium* hybrid plant named 'COADELBBL', substantially as described and illustrated herein.

* * * * *